United States Patent [19]

Iimura et al.

[11] 4,316,024
[45] Feb. 16, 1982

[54] DIOXO PIPERAZINE COMPOUNDS

[75] Inventors: Seiji Iimura, Tokyo; Jun Okumura, Yokohama; Takayuki Naito, Kawasaki, all of Japan

[73] Assignee: Bristol-Myers Company, New York, N.Y.

[21] Appl. No.: 187,273

[22] Filed: Sep. 15, 1980

[51] Int. Cl.³ .......................................... C07D 241/04
[52] U.S. Cl. ................................... 544/359; 544/366; 424/246; 544/27; 544/26
[58] Field of Search ........................ 544/366, 27, 359

[56] References Cited

U.S. PATENT DOCUMENTS

| | | | |
|---|---|---|---|
| 4,061,748 | 12/1977 | Yamara et al. | 424/246 |
| 4,087,424 | 5/1978 | Saikawa et al. | 260/268 C |
| 4,198,504 | 4/1980 | Naito et al. | 544/25 |
| 4,258,195 | 3/1981 | Shibuya et al. | 424/246 |

FOREIGN PATENT DOCUMENTS

| | | |
|---|---|---|
| 4570 | 10/1979 | European Pat. Off. |
| 51-70788 | 6/1976 | Japan |
| 51-113890 | 10/1976 | Japan |
| 52-36684 | 3/1977 | Japan |
| 52-39694 | 3/1977 | Japan |
| 52-87189 | 7/1977 | Japan |
| 52-106883 | 9/1977 | Japan |
| 52-151187 | 12/1977 | Japan |
| 53-15394 | 2/1978 | Japan |
| 53-18595 | 2/1978 | Japan |
| 53-44584 | 4/1978 | Japan |
| 54-48784 | 4/1979 | Japan |
| 54-52090 | 4/1979 | Japan |
| 54-119494 | 9/1979 | Japan |

OTHER PUBLICATIONS

Saikawa et al., Yakugaku Zasshi, 97,980 (1977).
Matsubara et al., Antimicrob Agents Chemother., 16, 731 (1979).
Saikawa et al., Yakugaku Zasshi 99,929 (1979).
The Peptides, vol. 1, pp. 105–108 (1965), Academic Press, NY.
Chemistry of the Amino Acids, vol. 2, 1027–1048 (1961), John Wiley & Sons, Inc.

*Primary Examiner*—Nicholas S. Rizzo
*Attorney, Agent, or Firm*—Herbert W. Taylor, Jr.

[57] ABSTRACT

Certain cephalosporins having a heterocyclicthiomethyl group at the 3-position such as cefoperazone are prepared by reacting a solution of a 7-acylamidocephalosporanic acid having a free amino group as part of said acyl substituent with about an equi-molar amount of the thiolester

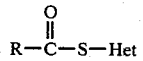

wherein —S-Het is the desired conventional heterocyclicthio group which displaces the 3-acetoxy group of the starting acid and

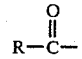

is the conventional acyl group which displaces a hydrogen on the free amino group which is part of the acyl substituent of the starting 7-acylamidocephalosporanic acid.

2 Claims, No Drawings

DIOXO PIPERAZINE COMPOUNDS

BACKGROUND OF THE INVENTION

1. Field of the Invention

The chemical processes of the present invention produce certain members of the class of antibacterial agents called cephalosporins.

2. Description of the Prior Art

Cefoperazone (T-1551), 7-[D(−)-α-(4-ethyl-2,3-dioxo-1-piperazinylcarboxamido)-α-(4-hydroxyphenyl)acetamido]-3-[(1-methyl-1H-tetrazol-5-yl)thiomethyl]-3-cephem-4-carboxylic acid, is a semisynthetic cephalosporin first reported by Toyama Chem. Ind. (Japan) and disclosed, for example, in general terms in U.S. Pat. No. 4,087,424 with a precursor acid named at column 40, line 57 of that patent. It has a broader spectrum of antibacterial activity than other cephalosporins including cefamandole and cefazolin and is significantly active against *Ps. aeruginosa, Ser. marcescens* and *Ent. cloacae* (ref. 15).

Cefoperazone is under clinical investigation (phase III) in Japan being developed by Toyama and in the U.S. by Pfizer. Because of its potentiality to become a promising product, various procedures have been reported for the preparation of cefoperazone (ref. 1–ref. 13). They are classified into four methods, A to D, as shown in Table 1.

TABLE 1

Published methods of cefoperazone (CPZ)

Method A: 7-N-Acylation of the 3-thiolated 7-ACA or its equivalents (ref. 1–ref. 10)

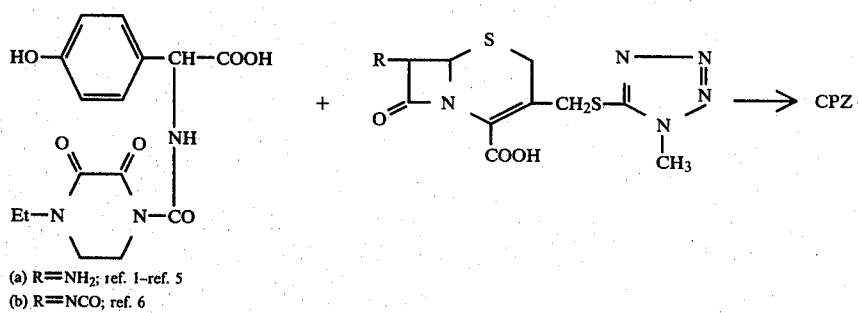

(a) R=NH₂; ref. 1–ref. 5
(b) R=NCO; ref. 6
(c) R=PhCH₂CONH, $\xrightarrow{TMSCl}$ $\xrightarrow{PCl_5}$ $\xrightarrow{MeOH}$ ; ref. 7–ref. 10

Method B: α-N-Acylation of the 3-thiolated 7-p-hydroxyphenylglycyl cephalosporin (ref. 11)

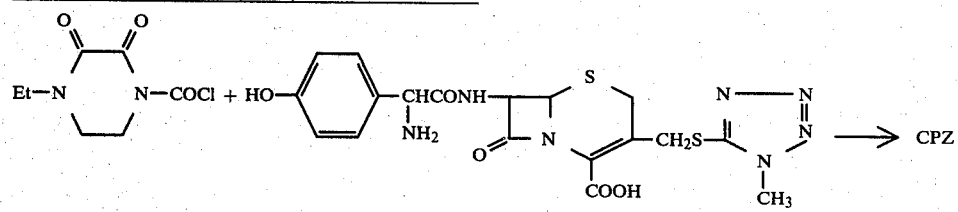

Method C: 3′-Thiolation of the 3′-acetoxy derivative (ref. 12)

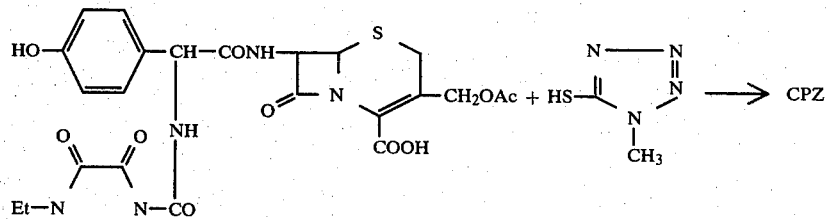

Method D: Cyclization to the dioxopiperazine ring (ref. 13)

TABLE 1-continued

Published methods of cefoperazone (CPZ)

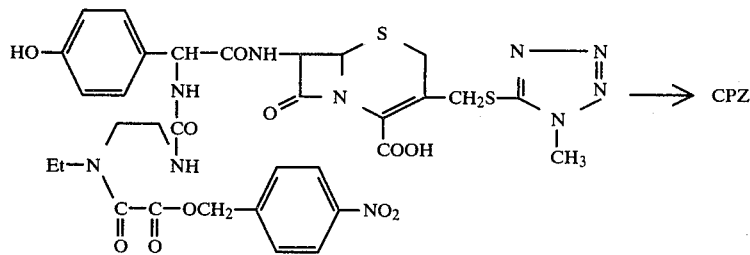

References
(1) I. Saikawa et al., Yakugaku Zasshi, 99, 929 (1979).
(2) Japan Kokai 51-70788 (6/18/76, Toyama).
(3) Japan Kokai 52-106883 (9/7/77, Toyama).
(4) Japan Kokai 54-48784 (4/17/79, Toyama).
(5) Japan Kokai 54-52090 (4/24/79, Toyama).
(6) Japan Kokai 53-18595 (2/20/78, Toyama).
(7) Japan Kokai 52-39694 (3/28/77, Toyama).
(8) Japan Kokai 52-151187 (12/15/77, Toyama).
(9) Japan Kokai 53-44584 (4/2/78, Toyama).
(10) Japan Kokai 53-15394 (2/13/78, Toyama).
(11) Japan Kokai 52-87189 (7/20/77, Toyama).
(12) Japan Kokai 51-113890 (10/7/76, Toyama).
(13) Japan Kokai 52-36684 (3/22/77, Toyama).
(14) I. Saikawa et al., Yakugaku Zasshi, 97, 980 (1977).
(15) N. Matsubara et al., Antimicrob. Agents Chemother., 16, 731 (1979).

The synthesis of peptides by activation of a carboxyl group using its thiolester has been reviewed in The Peptides, Volume I, Methods of Peptide Synthesis, Academic Press, N.Y. (1965) on pages 105–108 and in chemistry of the Amino Acids, Volume 2, John Wiley and Sons, Inc., N.Y. (1961) on pages 1027–1048.

In the field of cephalosporins it is common to make general reference to acylations of primary amino groups using an acid in the form of "an active ester or thiolester (e.g., with p-nitrophenol, 2,4-dinitrophenol, thiophenol, thioacetic acid)" as in column 8 of U.S. Pat. No. 4,198,504. That patent also provides examples of other patents disclosing the production of α-aminoarylacetamidocephalosporanic acids and refers to U.S. Pat. No. 4,061,748 for a disclosure of acylation of such compounds with an activated derivative of the acid having the formula

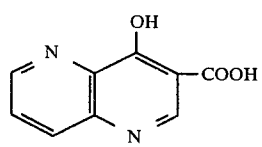

Derwent's Farmdoc abstract 78288B reports the reaction of 7-aminocephalosporanic acid with the thiolester having the formula

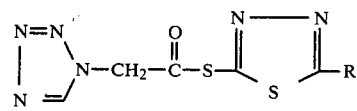

wherein R is hydrogen or methyl to produce cefazolin (where R is methyl) and ceftezole (where R is hydrogen) having the formula

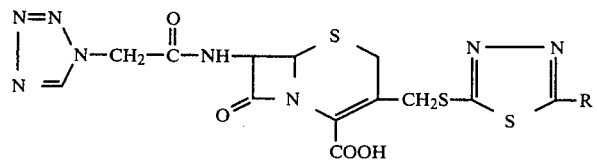

(and see also Farmdoc 75634 and European Patent Application 4570).

SUMMARY OF THE INVENTION

There is also provided by the present invention the process for the production in a single reaction of a cephalosporin having an acylamido group on the 7-sidechain at the 7-position and a heterocyclic-thiomethyl group at the 3-position which comprises reacting a solution of a 7-acylamidocephalosporanic acid having a free amino group as part of said acyl substituent, and preferably having a pH in the range of 6 to 8 which optionally contains a water-miscible, inert organic solvent such as acetone, at a temperature in the range of 20°–100° C. and preferably at about 55° C. for the period of time necessary to complete the reaction with about an equimolar amount, and preferably a small molar excess, of the thiolester

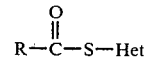

wherein —S-Het is the desired conventional heterocyclicthio group which displaces the 3-acetoxy group of the starting acid and

is the conventional acyl group which displaces a hydrogen on the free amino group which is part of the acyl substituent of the starting 7-acylamidocephalosporanic acid.

Preferred embodiments of this process are the above process in which the starting acid has the structure

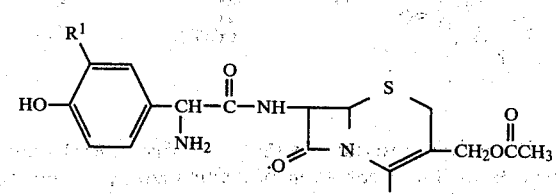

wherein $R^1$ is hydrogen, hydroxy, methyl, methoxy or chloro and the thiolester

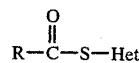

has the structure

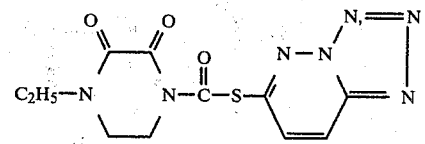

and the cephalosporin so produced has the structure

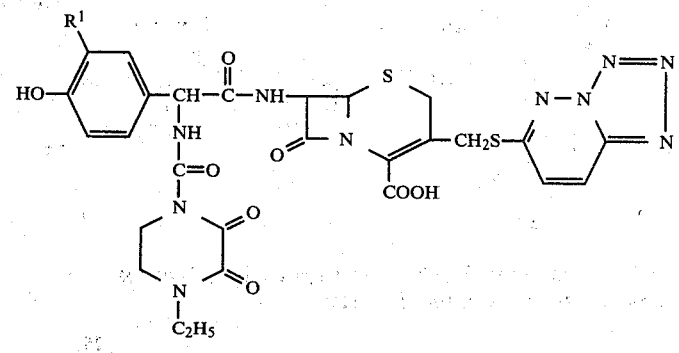

wherein $R^1$ has the same meaning as above and the above process in which the starting acid is p-hydroxy-cephaloglycine and the thiolester

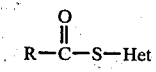

has the structure

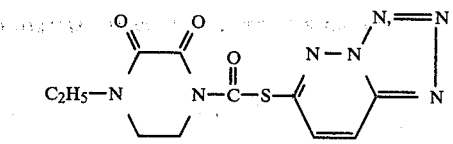

and the cephalosporin so produced has the structure

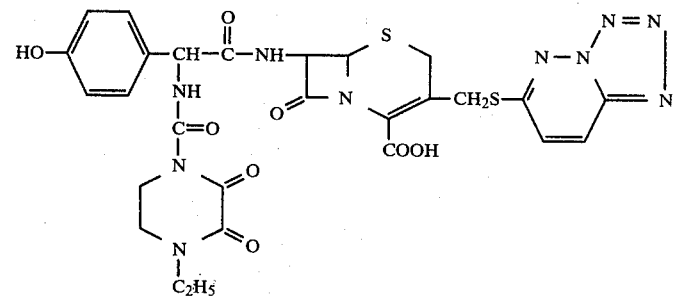

and the above process in which the starting acid is p-hydroxy-cephaloglycine and the thiolester

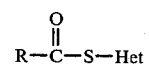

has the structure

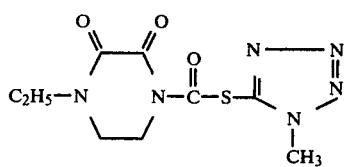

and the cephalosporin so produced has the structure

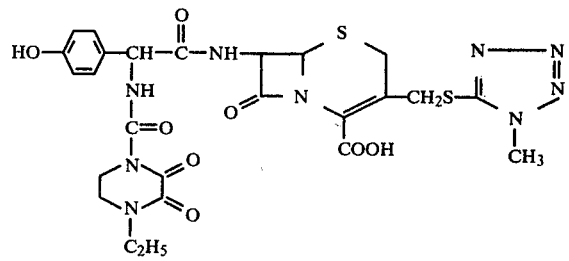

and the process in which the starting acid is p-hydroxycephaloglycine and the thiolester

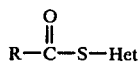

has the structure

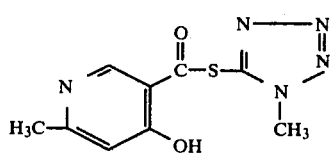

and the cephalosporin so produced has the structure

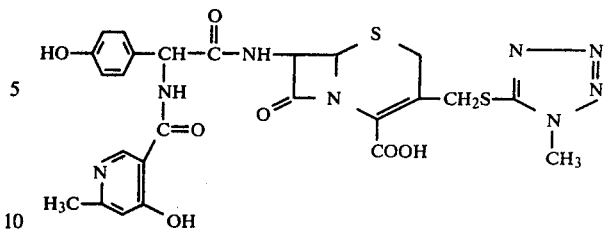

and the process in which the starting acid is p-hydroxycephaloglycine and the thiolester

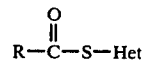

has the structure

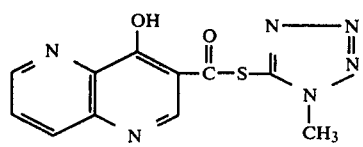

and the cephalosporin so produced has the structure

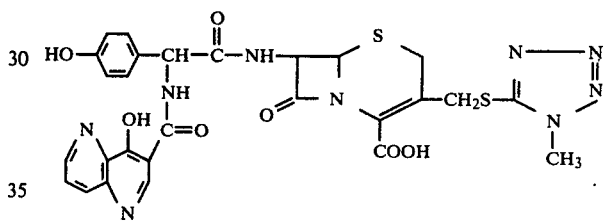

There is also provided by the present invention a new process for the preparation of cefoperazone, in which α-N-acylation and C-3′ thiolation are achieved simultaneously by the reaction of 7-[D(—)-α-amino-α-(p-hydroxyphenyl)acetamido]cephalosporanic acid (1) with 1-methyl-5-tetrazolyl 4-ethyl-2,3-dioxopiperazinocarbonylthiolate (2).

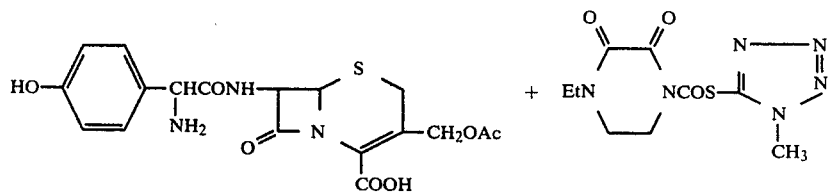

↓

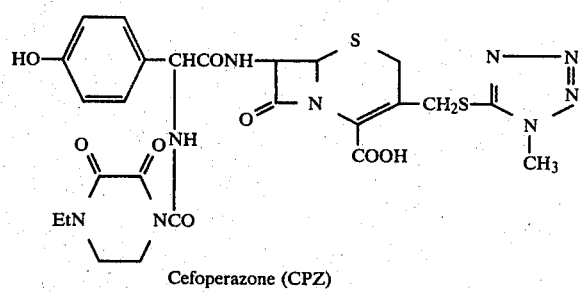

Cefoperazone (CPZ)

7-[D(−)-α-Amino-α-(p-hydroxyphenyl)acetamido]-cephalosporanic acid (1) was allowed to react with N-methyltetrazolyl 4-ethyl-2,3-dioxopiperazinylcarbonylthiolate (2) in a mixture of acetone and 0.1 M phosphate buffer (pH 7) heating at 50°–60° C. for 17 hours to give cefoperazone in a 52% yield by simultaneous reaction of α-N-acylation and 3'-thiolation. Cefoperazone thus obtained was identical with the authentic sample prepared by Method B of Table 1 in comparison of ir, uv, nmr and HPLC data. The thiolester 2 used in this preparation is a new compound. It was prepared by the reaction of 4-ethyl-2,3-dioxopiperazinylcarbonyl chloride (4) and 1-methyltetrazol-5-thiol (5a) in a 39% yield. When this reaction was performed with the tri-n-butyltin thiolate 5b, which was also a new compound, the yield of 2 was improved to 69%.

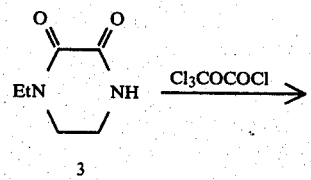

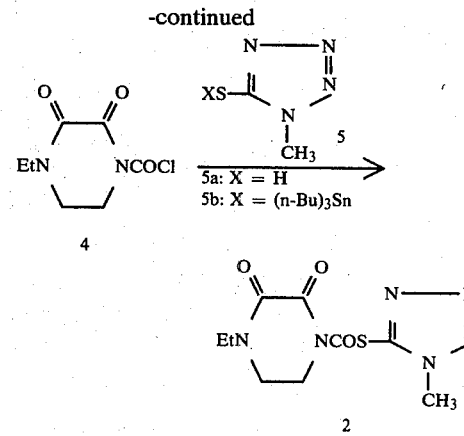

This procedure is also applicable to the preparation of 7-(α-N-acylamino-arylacetamido)-3-(thiolated-methyl)-cephems such as BB-S679, BB-S667 and BB-S724 which have the structures

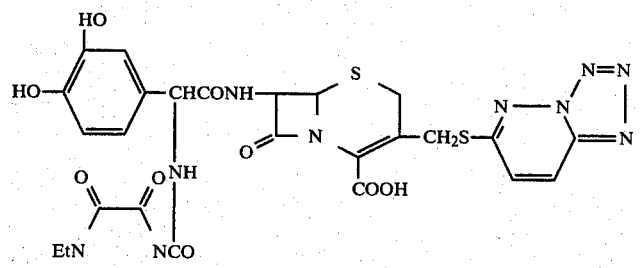

and

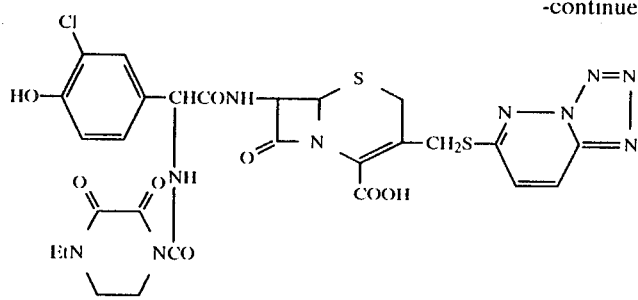

These three compounds do not form part of the present invention as they are disclosed and claimed by our colleagues and some of us in application U.S. Ser. No. 133,176 filed Mar. 24, 1980. These three compounds have the same utility and are used in the same fashion as cefaperazone.

PREPARATION OF STARTING MATERIALS sodium sulfate and evaporated yielding 3.9 g of the tri-n-butyltin derivative 5b. To a solution of 5b (3.9 g) in dry tetrahydrofuran (THF) was added the chloride 4 (2.0 g, 10 m moles) at room temperature and the mixture was stirred at the same temperature for 5 hours. The resulting solid was collected by filtration and crystallized from methylene chloride-ether yielding 1.95 g (69% from 5a) of the thiolester 2.

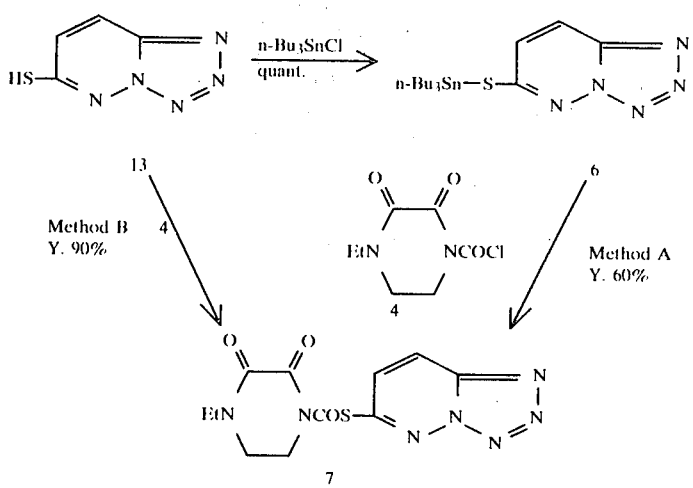

1-Methyltetrazol-5-yl 4-ethyl-2,3-dioxopiperazin-1-ylcarbonylthiolate (2)

(A) To a solution of 1-methyltetrazol-5-thiol (5a) (209 mg, 1.8 m moles) in dry THF was added 4-ethyl-2,3-dioxopiperazin-1-ylcarbonyl chloride (4)[14] (306 mg, 1.5 m moles) at −10° C. The mixture was stirred at −10° C. for 30 minutes and allowed to stand for 4 hours at room temperature. The resulting precipitate was collected by filtration and crystallized from methylene chloride-ether, yielding 166 mg (39%) of colorless needles (2).

m.p. 221°–224° C.

ir: $\nu_{max}^{KBr}$ 1715, 1680, 1670 cm$^{-1}$.

nmr: $\delta_{ppm}^{DMSO-d6}$ 1.12 (3H, t, J=7.5 Hz), 3.42 (2H, q, J=7.5 Hz), 3.5–4.0 (4H, m), 4.0 (3H, s).

Anal. Calcd. for $C_9H_{12}N_6O_3S$: C, 38.02; H, 4.25; N, 29.56; S, 11.28. Found: C, 38.16, 37.82; H, 4.05, 4.14; N, 29.47, 29.29; S, 11.18, 11.09.

(B) To a mixture of the thiol 5a (1.16 g, 10 m moles) and triethylamine (1.6 ml, 12 m moles) in carbon tetrachloride was added tri-n-butyltin chloride (3.25 g, 10 m moles) dropwise over a period of 10 minutes at room temperature and the mixture was stirred overnight. The reaction mixture was filtered and the filtrate was washed with 5% aqueous acetic acid (20 ml) and water (20 ml). The organic layer was dried over anhydrous

Tri-n-butyltin tetrazolo[1,5-b]pyridazin-6-mercaptide (6)

To an ice cooled solution of the thiol 13 (12.0 g, 78.3 m moles) and 13.5 ml (96.8 m moles) of triethylamine in 300 ml of methylene chloride was added dropwise with stirring a solution of n-butyltin chloride (25.4 g, 78.0 m moles) in 40 ml of the same solvent. The mixture was stirred at room temperature overnight and washed with 5% aqueous acetic acid (2×100 ml) and water (4×400 ml). After drying over sodium sulfate, the solvent was evaporated to give 34.7 g of 6 as a clear orange oil.

ir: $\nu_{max}^{film}$ 2970, 2940, 2880, 1605, 1540, 1470, 1430 cm$^{-1}$.

Tetrazolo[1,5-b]pyridazin-6-yl(4-ethyl-2,3-dioxopiperazin-1-yl)carbonylthiolate (7)

Method A

To an ice cooled solution of the mercaptide 6 (34.0 g, 77 m moles) in 150 ml of dry methylene chloride was added a solution of 4-ethyl-2,3-dioxopiperazinylcarbonyl chloride (4) (15.3 g, 75 m moles) in 100 ml of the same solvent with stirring for 30 minutes. The resulting suspension was stirred for an hour without cooling and the crystalline precipitates were collected by filtration. After washing with 200 ml of acetone, the pale yellow crystals were dried over $P_2O_5$ under reduced pressure to obtain 14.5 g (60%) of 7.

m.p. 209°–216° C. (dec.).

ir: $\nu_{max}^{KBr}$ 1705, 1685(sh), 1670(s), 1180 cm$^{-1}$.

nmr: $\delta_{ppm}^{DMSO-d_6}$ 1.13 (3H, t, J=7 Hz), 3.43 (2H, q, J=7 Hz), 3.65 (2H, m), 3.95 (2H, m), 7.97 (1H, d, J=9.5 Hz), 8.82 (1H, d, J=9.5 Hz).

Anal. Calcd. for $C_{11}H_{11}N_7O_3S$: C, 41.12; H, 3.45; N, 30.51; S, 9.98. Found: C, 40.91; 41.04, 41.00; H, 3.21, 3.29, 3.29; N, 30.08, 29.98, 30.19; S, 9.76, 9.85 (%).

Method B

To a solution of the thiol 13 (306 mg, 2.0 m moles) and 0.3 ml (2.2 m moles) of triethylamine in 10 ml of methylene chloride was added 512 mg (2.5 m moles) of the acid chloride 4 and the mixture was stirred at room temperature for 1.5 hours. The solid material was collected by filtration and washed with methylene chloride and dried over $P_2O_5$ under reduced pressure to give 580 mg (90%) of the thiolester 7.

Other thiolester starting materials are prepared by replacing the 1-methyltetrazol-5-thiol in any of the above procedures with an equimolar weight of another mercaptan.

HP-20 is a macroreticular adsorbent resin in the form of insoluble beads of porous polymer. They are macroporous-nonionic, cross-linked polystyrene polymers.

DESCRIPTION OF THE PREFERRED EMBODIMENTS

Example 1

Cefoperazone;

7-[D(−)-α-(4-Ethyl-2,3-dioxo-1-piperazinylcarboxamido]-3-[(1-methyl-1H-tetrazol-5-yl)thiomethyl]-3-cephem-4-carboxylic acid A mixture of 7-[D(−)-p-hydroxyphenylglycylamido]-cephalosporanic acid (1) (209 mg, 0.5 m mole), sodium bicarbonate (84 mg, 1 m mole) and the thiol ester 1-methyltetrazol-5-yl 4-ethyl-2,3-dioxopiperazin-1-ylcarbonylthiolate (2) (170 mg, 0.6 m mole) in 0.1 M phosphate buffer (pH 7, 5 ml) and acetone (5 ml) was heated at 50°–60° C. for 17 hours. Acetone was removed by evaporation. The aqueous residue was acidified with N HCl. The resulting precipitate was collected by filtration, washed with water (5 ml) and dried to yield 169 mg (52%) of cefoperazone.

m.p. 170°–175° C. (dec.) (lit[1]) 169°–171° C. (dec.).

ir: $\nu_{max}^{KBr}$ 1780, 1710, 1670, 1610, 1520 cm$^{-1}$.

uv: $\lambda_{max}^{ph7Buffer}$ 226 nm (ε, 21700), 263 nm (ε, 12200).

nmr: $\delta_{ppm}^{DMSO-d_6+D_2O}$ 1.07 (3H, t, J=7 Hz, N-CH$_2$CH$_3$), 3.0–4.4 (10H, m, 2-H, 3-CH$_2$, piperazine-CH$_2$, N-CH$_2$CH$_3$), 3.90 (3H, s, N-CH$_3$), 4.93 (1H, d, J=5 Hz, 6-H), 5.40 (1H, s, CH-CO), 5.63 (1H, d, J=5 Hz, 7-H), 6.68 (2H, d, J=9 Hz, phenyl-H), 7.18 (2H, d, J=9 Hz, phenyl-H).

EXAMPLE 2

Preparation of BB-S679

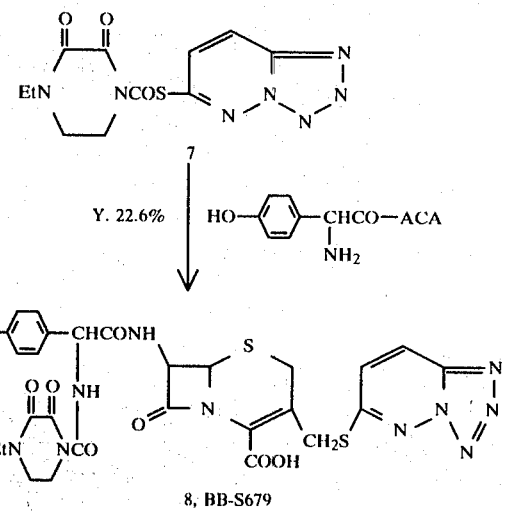

8, BB-S679

Sodium 7-[D-α-(4-ethyl-2,3-dioxo-1-piperazinocarboxamido)α-(4-hydroxyphenyl)acetamido]-3-(tetrazolo[1,5-b]pyridazin-6-ylthiomethyl)-3-cephem-4-carboxylate (8, BB-S679)

To a stirred solution of 7-[D-α-amino-α-(4-hydroxyphenyl)acetamido]cephalosporanic acid (13.9 g, 33 m moles) and sodium bicarbonate (5.9 g, 37.3 m moles) in 240 ml of phosphate buffer (0.2 M, pH 7.0) was added the thiolester 7 (12.0 g, 37.3 m moles) in portions during 15 minutes. The mixture was heated at 30°–65° C. for an hour and the resulting clear solution was further heated at 74°–76° C. for 2.5 hours. After cooling, the solution was treated with charcoal and filtered through diatomaceous earth (Celite) and the filtrate was cooled in ice-water and then acidified to pH 2 with 20% (v/v) phosphoric acid.

The resulting precipitates were isolated by filtration and dried over $P_2O_5$ under reduced pressure to give 9.1 g of tan powder.

The powder was dissolved in 70 ml of dimethylformamide and was mixed with 14 ml of 1 M sodium 2-ethylhexanoate (in anhydrous ethyl acetate) to give a solution which was added dropwise to stirred ethyl acetate (2.1 l.) and the precipitated cephalosporin was collected by filtration. After drying, the crude sodium salt was dissolved in water (ca. 50 ml), chromatographed on an HP-20 column (ca. 600 ml) and eluted with water (2.5 l.) and 50% methanol (3 l.) successively. The fractions containing 8 were collected, concentrated and lyophilized to give 5.26 g (22.6%) of 8 as pale yellow powder.

m.p. 197°–202° C. (dec.).

ir: $\nu_{max}^{KBr}$ 1763, 1710, 1675, 1600, 1515 cm$^{-1}$.

uv: $\lambda_{max}^{H_2O}$ 233.5 nm (ε, 29500), 268 nm (ε, 15900), 310 nm (ε, 5600).

nmr: $\delta_{ppm}^{DMSO-d_6}$ 1.1 (3H, t, J=7.5 Hz), 3.1–3.7 (9H, br, m), 3.82 (1H, br), 4.38 (1H, br), 4.84 (1H, d, J=4.5 Hz), 5.35–5.52 (2H, m), 6.6 (2H, d, J=8 Hz), 7.11 (2H, d, J=8 Hz), 7.60 (1H, d, J=10 Hz), 8.52 (1H, d, J=10 Hz).

Preparation of BB-S667

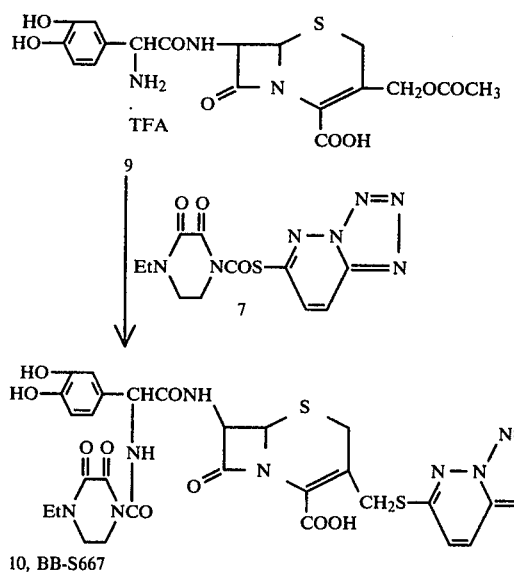

7-[D-α-(4-Ethyl-2,3-dioxo-1-carboxamido)-α-3,4-dihydroxyphenylacetamido]-3-(tetrazolo[1,5-b]pyridazin-6-ylthiomethyl)-3-cephem-4-carboxylic acid (10, BB-S667)

A mixture of 551 mg (1 m mole) of 7-[D-α-amino-α-(3,4-dihydroxyphenyl)acetamido]cephalosporanic acid trifluoroacetate (9), 480 mg (1.5 m moles) of the thiolester 7 and 252 mg (3 m moles) of sodium bicarbonate in 10 ml of 0.1 M phosphate buffer solution (pH 7.0) was stirred at 52° C. for 12 hours. The solution was extracted with ethyl acetate and the aqueous layer was adjusted to pH 3 with dil. hydrochloric acid. The resulting precipitate was collected by filtration, washed with water and dried in vacuo over $P_2O_5$ to give 325 mg (46.5%) of the title compound 10.

ir: $\nu_{max}^{KBr}$ 1780, 1720, 1680, 1530, 1450, 1390, 1190 $cm^{-1}$.

Preparation of BB-S724

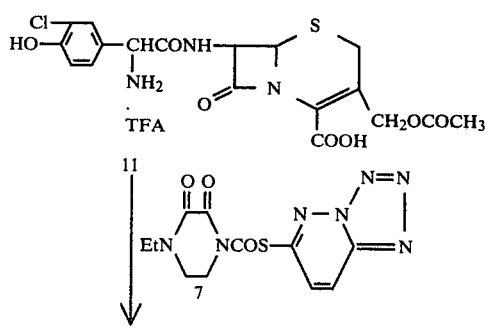

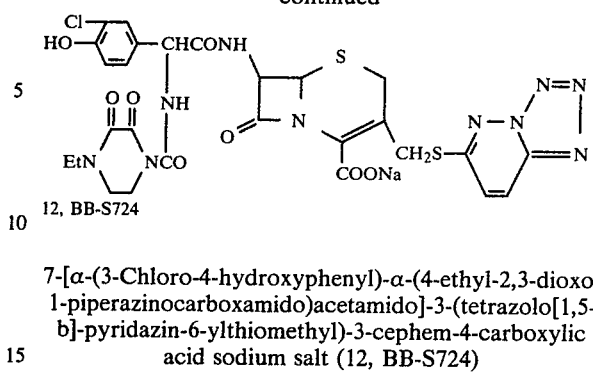

7-[α-(3-Chloro-4-hydroxyphenyl)-α-(4-ethyl-2,3-dioxo-1-piperazinocarboxamido)acetamido]-3-(tetrazolo[1,5-b]-pyridazin-6-ylthiomethyl)-3-cephem-4-carboxylic acid sodium salt (12, BB-S724)

A mixture of 7-[α-amino-α-(3-chloro-4-hydroxyphenyl)acetamido]-3-acetoxymethyl-3-cephem-4-carboxylic acid TFA salt (11, 349 mg, 0.61 m mole), tetrazolo[1,5-b]-pyridazin-6-yl 4-ethyl-2,3-dioxopiperazin-1-yl-carbonylthiolate (7, 295 mg, 0.92 m mole) and sodium bicarbonate (154 mg, 1.84 m moles) in 0.1 M phosphate buffer (pH 7, 8 ml) and acetone (8 ml) was heated at 50°-55° C. for 24 hours. Acetone was removed by evaporation. The aqueous residue was washed with ethyl acetate (5 ml) and acidified with 6 N HCl. The resulting precipitate was collected by filtration, yielding 343 mg of a crude product, 300 mg of which was redissolved in water by adding sodium bicarbonate. The solution was chromatographed on HP-20 (30 ml), eluted with water, 10% MeOH, 30% MeOH and 50% MeOH, successively. The eluates of 10% MeOH, 30% MeOH and 50% MeOH were combined, concentrated to a small volume and lyophilized to afford 203 mg (Y. 47%) of the title compound 12.

m.p. >200° C. (dec.).

ir: $\nu_{max}^{KBr}$ 1760, 1710, 1660, 1600, 1500, 1440, 1400, 1360, 1290, 1190, 1110, 1020 $cm^{-1}$.

uv: $\lambda_{max}^{pH7Buffer}$ 233 nm (ε, 17500), 267 nm (sh), (ε, 9900), 298 nm (sh) (ε, 3100).

nmr: $\delta_{ppm}^{DMSO-d6}$ 1.08 (3H, t, J=7 Hz), 4.86 (1H, d, J=4.5 Hz), 5.3–5.6 (2H, m), 6.8–7.4 (3H, m), 7.72 (1H, d, J=10.5 Hz), 8.55 (1H, d, J=10.5 Hz).

This invention is capable of industrial application.

We claim:

1. The compound having the structure

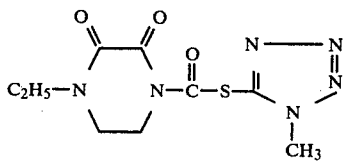

2. The compound having the structure

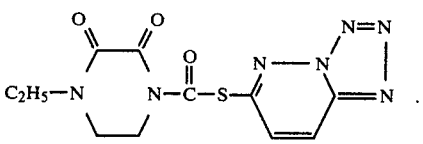

* * * * *